United States Patent [19]

Oh

[11] Patent Number: 4,623,352

[45] Date of Patent: Nov. 18, 1986

[54] PROTRUSIO CUP

[76] Inventor: Indong Oh, 851 Lyndon St., South Pasadena, Calif. 91030

[21] Appl. No.: 587,287

[22] Filed: Mar. 7, 1984

Related U.S. Application Data

[63] Continuation-in-part of Ser. No. 340,024, Jan. 18, 1982, Pat. No. 4,437,193.

[51] Int. Cl.$^4$ ............................................. A61F 2/34
[52] U.S. Cl. ................................................... 623/23
[58] Field of Search .................... 3/1, 1.9, 1.91, 1.912, 3/1.913; 128/92 C, 92 CA

[56]  References Cited

U.S. PATENT DOCUMENTS

| | | |
|---|---|---|
| D. 232,004 | 7/1874 | Amstutz . |
| D. 232,005 | 7/1874 | Farling . |
| D. 235,377 | 6/1875 | Medcraft . |
| 3,608,096 | 9/1971 | Link . |
| 3,722,002 | 3/1973 | Charnley . |
| 3,829,904 | 8/1974 | Ling et al. . |
| 3,903,549 | 9/1975 | Deyerle . |
| 3,922,726 | 12/1975 | Trentani et al. .................. 3/1.912 |
| 4,327,449 | 5/1982 | Charnley . |
| 4,437,193 | 3/1904 | Oh ...................................... 3/1.912 |

FOREIGN PATENT DOCUMENTS

| | | | |
|---|---|---|---|
| 0065482 | 11/1982 | European Pat. Off. ............ | 3/1.912 |
| 2903366 | 8/1979 | Fed. Rep. of Germany ....... | 3/1.912 |
| 2932744 | 2/1980 | Fed. Rep. of Germany ....... | 3/1.912 |
| 7202254 | 8/1973 | Netherlands ......................... | 3/1.912 |

OTHER PUBLICATIONS

"Protrusio Shell Surgical Technique", *Howmedica Surgical Techniques,* Indong Oh, M.D., et al., Howmedica, Inc., 1978.

*Primary Examiner*—Richard J. Apley
*Assistant Examiner*—David Isabella
*Attorney, Agent, or Firm*—Gordon L. Peterson

[57]  ABSTRACT

A protrusio cup for implantation in the acetabulum, including an acetabular cup and a protrusio shell mounted on the acetabular cup by interlocking grooves and projections. The acetabular cup has a hemispherical bearing surface which terminates in a part-conical surface. The bearing surface and the part-conical surface are rotated through an angle to reduce the likelihood of dislocation and to increase the range of motion.

20 Claims, 9 Drawing Figures

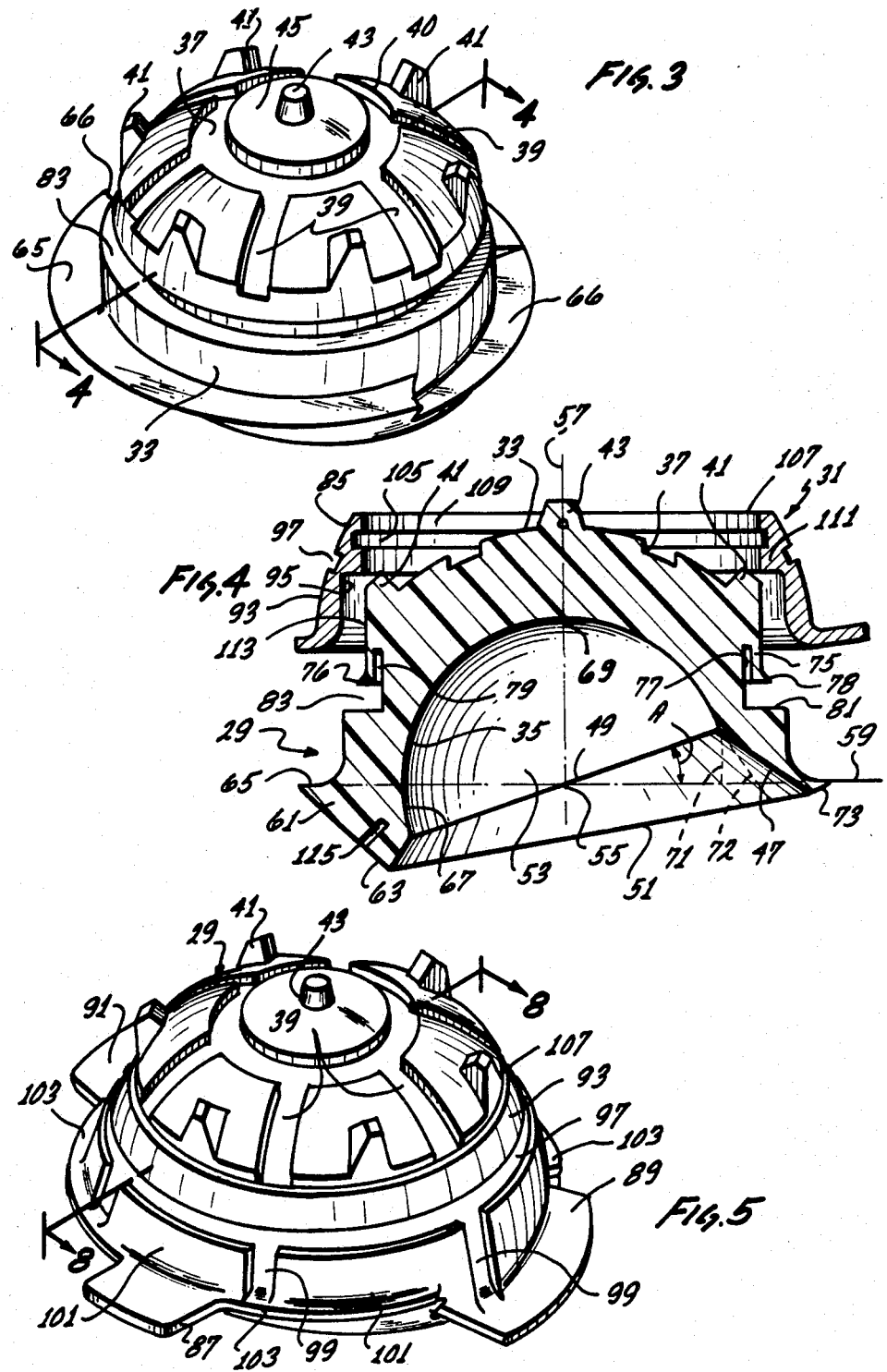

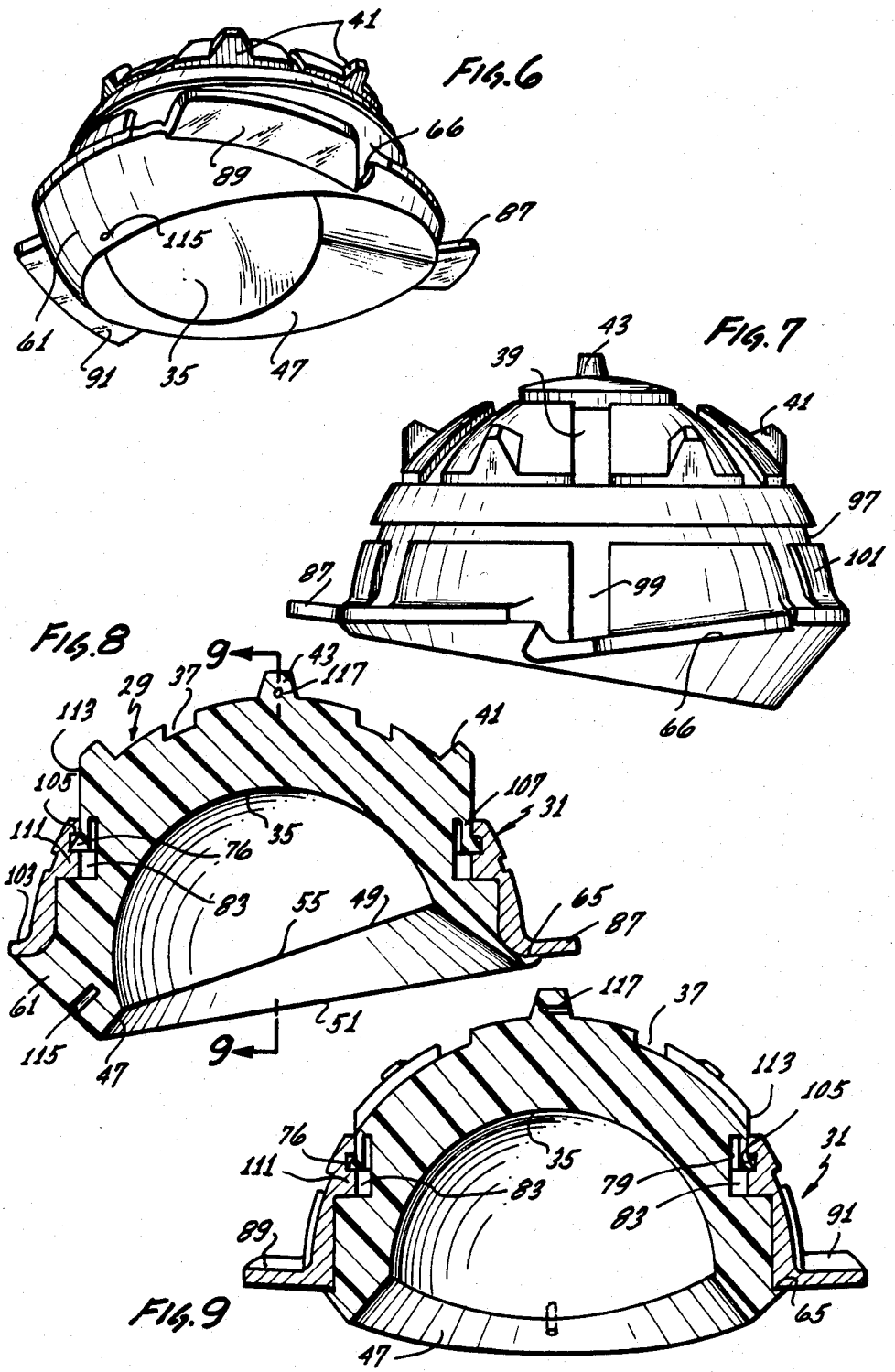

PROTRUSIO CUP

This application is a continuation-in-part of application Ser. No. 340,024 filed Jan. 18, 1982, now U.S. Pat. No. 4,437,193 and entitled Protrusio Cup.

BACKGROUND OF THE INVENTION

A hip joint comprises a socket or acetabulum and a femoral head or ball received in the acetabulum. Thus, the hip joint is a ball and socket joint which provides universal motion.

Various diseases, such as osteoarthritis, attack the hip joint and, when this occurs, it may be necessary to utilize an appropriate hip joint prosthesis to replace the femoral head and the acetabulum. This may also be necessary in other circumstances, such as in the case of certain hip joint fractures.

Deterioration of the acetabulum requires that an acetabular cup be mounted in the acetabulum to provide a socket for slidably receiving the prosthetic femoral head. If the medial wall of the acetabulum is sufficiently weakened, it may be necessary to protect this wall with a protrusio shell. The protrusio shell has one or two flanges for seating on the ilium, the ischium and the pubis. Accordingly, the medial thrust from the femoral head is dispersed through the flanges to the ilium, ischium and pubis.

One problem with hip joint prostheses is dislocation, i.e., removal of the femoral head from the acetabular cup. As described in my above-identified copending application, to help prevent dislocation, the acetabular cup may have an overhanging portion or extension at least in the superior-posterior region. Although a construction of this type is quite effective in reducing the likelihood of dislocation, it may not provide the desired range of motion.

As set forth in my copending application, it is desirable to implant the protrusio cup as a single unit in a one-step surgical technique. This, however, requires the preattachment of the protrusio shell and the acetabular cup in a predetermined orientation relative to each other. Previously attempted techniques for attaching the protrusio shell and the acetabular cup have created assembly problems that have resulted in damage to, and consequent scrapping of, some of the acetabular cups.

SUMMARY OF THE INVENTION

This invention provides an increased range of motion for a femoral prosthesis which includes a protrusio cup of the type which has an overhang at least in the superior-posterior region. Accordingly, the protrusio cup of this invention both resists dislocation and allows a good range of motion. In addition, the protrusio cup has features which tend to provide even greater resistance to dislocation than is afforded by the overhang itself. However, if dislocation should occur, the protrusio cup has surfaces which tend to guide the femoral head back into the protrusio cup.

This invention also provides for the easy, yet very secure, attachment of the protrusio shell to the acetabular cup. In this regard, the acetabular cup has a resilient skirt on its exterior and a wall spaced radially inwardly of the skirt to define a gap between the skirt and the wall so that the skirt can flex radially inwardly. The protrusio shell can be mounted on the acetabular cup by interlocking means on the protrusio shell and the acetabular cup. At least a portion of such interlocking means is on the skirt.

The interlocking means may comprise, for example, one or more cooperating ribs and grooves on the acetabular cup and the protrusio shell. In a preferred construction, the interlocking means includes a rib on the skirt projecting radially outwardly and a groove on the protrusio shell for receiving the rib. In addition, in a preferred construction, the interlocking means includes a groove on the acetabular cup adjacent the skirt and a rib on the protrusio shell.

To help resist dislocation, the acetabular cup has a projection that extends beyond one end of the protrusio shell with the projection being greater on one side of the acetabular cup than on the other to define an overhang at least on such one side of the acetabular cup. The acetabular cup has an inner concave bearing surface of generally part-spherical configuration defining a cavity with the bearing surface being adapted to receive a femoral head and slidably cooperate therewith. The bearing surface is oriented to provide an increased range of motion for the femoral head without materially increasing the likelihood of dislocation. To further increase the range of motion, the acetabular cup has a part-conical surface which intersects the bearing surface and which extends radially outwardly as it extends away from the bearing surface. This conical surface has a cone angle.

To further increase the range of motion and to provide other advantages, the cone angle is rotated generally away from the side on which the overhang is the greatest. This positions the conical surface so as to allow the neck of the femoral component a wide range of motion. In addition, with the cone at this angle, the part-conical surface provides a long lead-in which would tend to guide the femoral head back toward the cavity defined by the bearing surface if dislocation should occur. Finally, the part-conical surface tends to provide essentially surface contact with the neck of the femoral component rather than point contact, and accordingly, the femoral component is less likely to act as a lever to force or pop the femoral head out of the acetabular cup.

Preferably, the part-conical surface intersects the bearing surface to define a first plane, and the part-conical surface terminates in a second plane which is non-parallel to the first plane. The cone angle, in a preferred construction, is rotated in the direction in which the distance between the planes increases.

The acetabular cup has grooves defining segments for interlocking with the bone cement which is used to retain the protrusio cup in the acetabulum. To prevent loss of interlocking strength at those regions of the acetabular cup which are covered by the protrusio shell, the protrusio shell may also be provided with grooves which define segments for interlocking with the bone cement.

A radiopaque marker can be embedded in a central or maximum region of the overhang so that the overhang can be accurately located on an X ray. Also, the acetabular cup and protrusio shell can be locked against relative rotation about a polar axis by providing notches in a flange of the acetabular cup for cooperating with at least two flanges of the protrusio shell.

The invention, together with additional features and advantages thereof, may best be understood by reference to the following description taken in connection with the accompanying illustrative drawing.

BRIEF DESCRIPTION OF THE DRAWING

FIG. 3 is an isometric view of the acetabular cup.

FIG. 4 is an exploded sectional view taken generally along line 4—4 of FIG. 3 showing the acetabular cup and the protrusio cup in position for assembly.

FIGS. 5 and 6 are isometric views of the protrusio cup taken from different angles.

FIG. 7 is an elevational view of the protrusio cup.

FIGS. 8 and 9 are sectional views of the protrusio cup taken generally along lines 8—8 of FIG. 5 and 9—9 of FIG. 8, respectively.

DESCRIPTION OF THE PREFERRED EMBODIMENT

Figure 1:
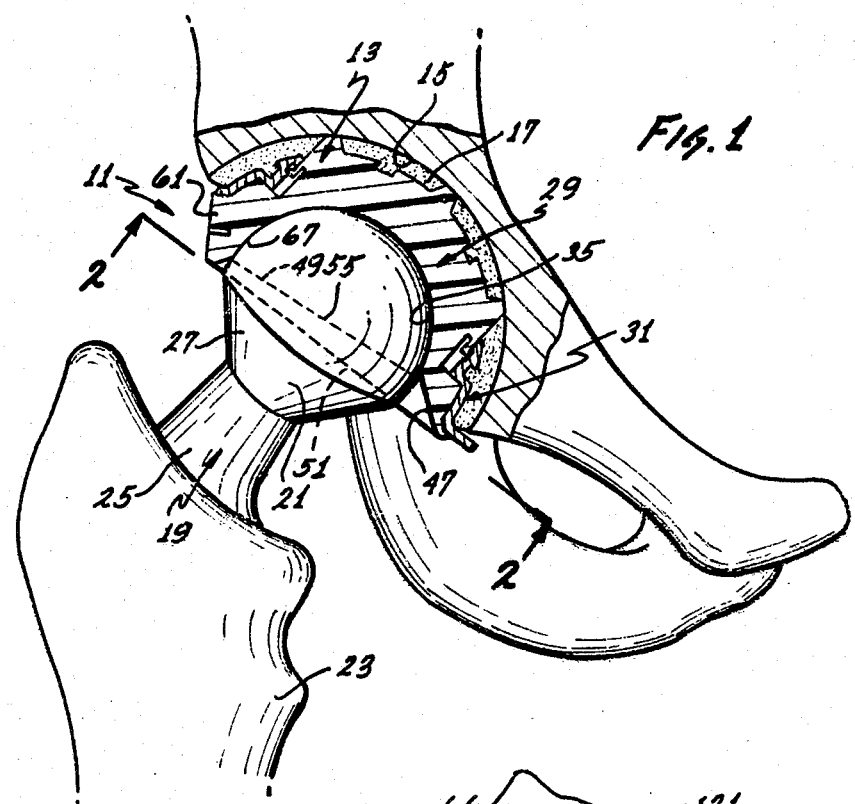
FIG. 1 is a front elevational view partially in section showing a hip joint prosthesis for the right hip which includes one preferred embodiment of the protrusio cup of this invention.

FIG. 1 shows a hip joint prosthesis 11 which includes a protrusio cup 13 retained in the acetabulum 15 by bone cement 17 and a femoral component 19 having a femoral head 21 slidably received within the protrusio cup 13. The protrusio cup can be used with femoral components of various different constructions. The femoral component 19, which is shown by way of example, also comprises a stem (not shown) which is inserted into the femur 23 and a neck 25 for joining the femoral head 21 to the stem. The femoral head 21 is essentially spherical, except for one or more conical portions 27 adjacent the neck 25.

The protrusio cup 13 comprises an acetabular cup 29 and a protrusio shell 31. The acetabular cup 29 is preferably molded of a suitable biocompatible plastic material, such as polyethylene. Although the acetabular cup 29 is of approximately hemispherical configuration, it is, in the preferred embodiment, not geometrically hemispherical in that, as set forth more particularly hereinbelow, it extends for more than 180 degrees and its outer surface is irregular. Although the acetabular cup 29 of this invention is particularly adapted for use with the protrusio shell 31, it can be used without a protrusio shell or with protrusio shells other than the shell 31.

The acetabular cup 29 (FIGS. 3 and 4) has an outer surface 33 with a generally part-spherical contour and an inner concave bearing surface 35 of part-spherical configuration adapted to receive the femoral head 21. The surface 35 and the spherical portions of the surface 33 are concentric. To provide a better interlock with the cement 17, the outer surface 33 is preferably of irregular configuration and for this purpose has an annular latitude groove 37 (FIG. 3) and a plurality of longitude grooves 39 which intersect the latitude groove to define segments 40 (FIG. 3). A plurality of pods or spacer lugs 41 is arranged in a ring with each of the lugs 41 being on a segment 40 intermediate an adjacent pair of the longitude grooves 39. In addition, a spacer lug 43 is provided on a polar segment 45 coaxially with the annular latitude groove 37.

As shown in FIG. 1, these lugs 41 and 43 engage the wall of the acetabulum 15 to provide an even thickness of the cement 17. In addition, the spacer lugs 41 and 43 transfer force to the bone and aid in properly positioning the protrusio cup 13 within the acetabulum 15.

To provide for a bearing surface of maximum area without capturing the head 21, the bearing surface 35 is preferably hemispherical. In the preferred embodiment illustrated, the bearing surface 35 intersects a part-conical surface 47 along a first or inner plane 49. The part-conical surface 47 extends radially outwardly as it extends away from the inner plane 49 and terminates outwardly in a second or outer plane 51. In the preferred embodiment illustrated, the planes 49 and 51 are nonparallel and they diverge or separate as they extend to the right as viewed in FIG. 4. Thus, the part-conical surface is truncated at an angle so that the part-conical surface 47 is shorter along one side of the acetabular cup than the other. The bearing surface 35 and the part-conical surface 47 cooperate to define a cavity 53 which opens at a mouth at the outer plane 51.

Figure 2:
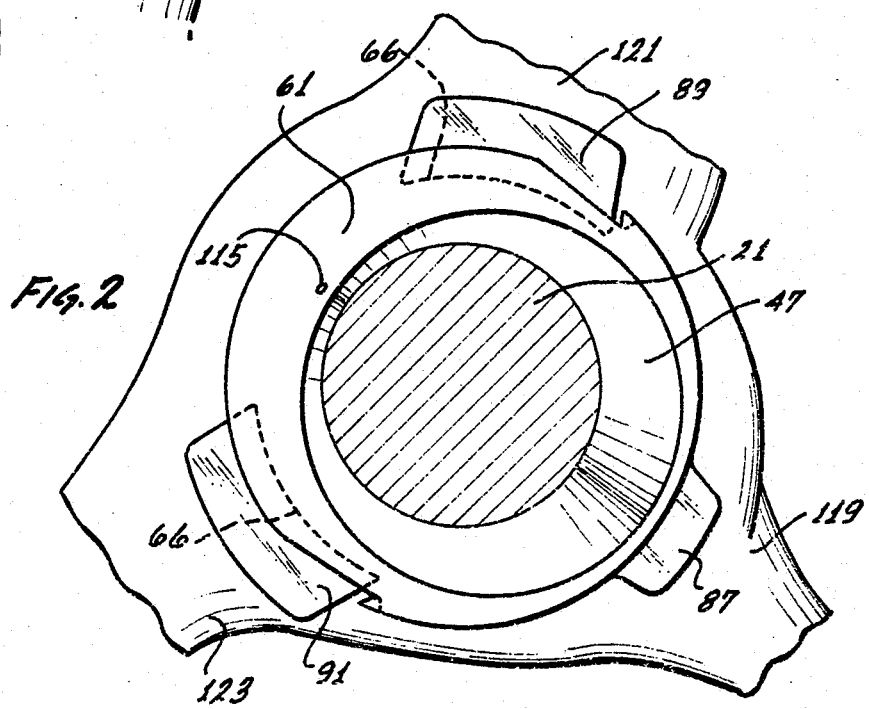
FIG. 2 is an enlarged, fragmentary sectional view taken generally along line 2—2 of FIG. 1.

The spherical portions of the outer surface 33 and the bearing surface 35 have a common center 55 in the inner plane 49. A polar axis 57 extends from the center 55 through the center of the polar segment 45 and the lug 43, and a transverse reference plane 59 extends perpendicular to the polar axis 57 through the center 55 to define above the plane a roughly hemispherical section of the acetabular cup 29. The acetabular cup 29 projects below the reference plane 59 to define an overhang 61. Specifically, the overhang 61 lies between the reference plane 59 and the outer plane 51. Thus, the overhang has its maximum extension at the left side of the acetabular cup 29 as viewed in FIG. 4 and its minimum extension on the right side of the acetabular cup as viewed in FIG. 4. The overhang 61 is defined on the exterior of the acetabular cup by a part-conical surface 63 and by a generally annular shoulder 65 which lies essentially in the reference plane 59. The shoulder 65 has notches 66 (FIGS. 2, 6 and 7).

As shown in FIG. 4, the inner plane 49 defines an angle "A" with the reference plane 59. In other words, both the inner plane 49 and the hemispherical bearing surface 35 are rotated counterclockwise as viewed in FIG. 4 through the angle "A" out of the reference plane 59. Accordingly, an overhanging section 67 of the bearing surface 35 projects below (as viewed in FIG. 4) the reference plane 59. As explained more fully hereinbelow, the overhanging section 67 is useful in resisting dislocation. Conversely, the bearing surface 35 on the side remote from the overhanging section 67 lies above (as viewed in FIG. 4) the reference plane 59. The overhanging section 67 and the portion of the part-conical surface 47 below the reference plane 59 define the inner surface of the overhang 61.

The part-conical surface 47 has an apex 69 which lies on the bearing surface 35 at the polar axis 57. The entire cone, including the part-conical surface 47, is rotated counterclockwise about the apex 69 through an angle equal to the angle "A" from the position that it would occupy if the polar axis 57 were to bisect the cone angle; i.e., the angle at the apex 69.

The rotation of the bearing surface 35 and the part-conical surface 47 provides for an increased range of motion. For example, if the bearing surface 35 extended all the way to the reference plane 59 at the side of the bearing surface remote from the overhang 61 as shown by the dashed line 71 in FIG. 4, the range of motion would be reduced. Similarly, if the cone were not rotated, the part-conical surface 47 would lie along dashed line 72 and the range of motion would be correspondingly reduced. If the part-conical surface 47 and the bearing surface 35 are rotated in the same direction through the same angle, then the neck 25 (FIG. 1) will make essentially line contact with the surface 47 at the limit of its travel which reduces the likelihood of dislocation. For example, the angle "A" may be about 17 degrees.

The outer plane 51 may form various different angles with the reference plane 59, and in the embodiment illustrated, the angle formed between them is 10 degrees. In this embodiment, the overhang 61 tapers to a thin flange 73 diammetrically across from the location at which the overhang 61 has its maximum dimension.

The acetabular cup 29 has a resilient, annular, continuous skirt 75 on its exterior and an annular rib projecting radially outwardly of the skirt. The rib 76 has a conical cam surface 78 which diverges as it extends downwardly. The acetabular cup 29 has a wall 77 spaced inwardly of the skirt to define an annular gap 79 between the skirt and the wall so that the skirt can flex radially inwardly. The skirt 75 terminates downwardly in a surface which cooperates with the portions of the wall 77 and with a shoulder 81 to form surface means which define an annular groove 83.

The protrusio shell 31 is preferably integrally constructed of a suitable biocompatible metal. The protrusio shell 31 comprises an annular segment 85 (FIG. 4) and three flanges 87, 89 and 91 (FIG. 2) projecting radially outwardly from the lower or wide end of the annular segment. The annular segment 85 has a part-spherical outer surface 93 and an inner surface 95. The protrusio shell 31 is open at both ends, and the outer surface has an annular, circumferentially extending latitude groove 97 and a number of longitude grooves 99 equal to the number of the longitude grooves 39. The grooves 97 and 99 cooperate to define segments 101 (FIG. 5). The flanges 87, 89 and 91 are spaced circumferentially, and radially short ledges 103 extend circumferentially between adjacent flanges. The centers of the flanges 87, 89 and 91 are preferably equally spaced, and the circumferential dimension of the flange 87 is preferably less than the circumferential dimension of the other two flanges.

An annular groove 105 is provided in the inner surface 95 adjacent an open end 107 of the protrusio shell 31. The groove 105 is defined by spaced annular ribs 109 and 111 on the inner surface 95.

The protrusio shell 31 is mounted on the acetabular cup 29 as shown in FIGS. 5-9. The mounting means for this purpose includes interlocking means formed by the rib 76 of the skirt 75, the groove 105, the groove 83, and the rib 111. As shown in FIGS. 8 and 9, the rib 76 is received in the groove 105, and the rib 111 is received within the groove 83 to interlock the protrusio shell 31 and the acetabular cup 29. In addition, the flanges 87, 89 and 91 and the ledges 103 are seated on the shoulder 65 of the acetabular cup 29 when the protrusio shell 31 is mounted on the acetabular cup 29 by the interlocking means. In addition, the flanges 89 and 91 are seated in the notches 66, respectively, to at least assist in preventing relative rotation between the protrusio shell 31 and the acetabular cup 29 about the polar axis 57. Of course, the interlocking means of this invention can be combined with other means, such as other interlocks or an adhesive, for mounting the protrusio shell 31 on the acetabular cup 29.

The protrusio shell 31 can be mounted on the acetabular cup 29 by pushing the protrusio shell downwardly from the position shown in FIG. 4 over the acetabular cup. For this purpose, the acetabular cup 29 has a cylindrical surface 113 extending from the rib 76 upwardly as viewed in FIG. 4, and the inner surface of the ribs 109 and 111 of the protrusio shell 31 are also cylindrical and sized to slip over the cylindrical surface 113. As the protrusio shell 31 moves downwardly over the cylindrical surface 113, the lower edge of the rib 111 contacts the rib 76 and, in particular, the conical cam surface 78 so that further advancing movement of the protrusio shell cams and flexes the skirt 75 radially into the gap 79 to allow the rib 111 to slip past the rib 76 and into the groove 83. This also allows the rib 76 to enter the groove 105 as shown in FIG. 8.

With the protrubio shell 31 mounted on the acetabular cup 29, the longitude grooves 39 of the acetabular cup are in alignment with the longitude grooves 99 of the protrusio shell. The acetabular cup 29 projects through the open end 107 as shown, for example, in FIGS. 5 and 7-9.

To permit the position of the overhang 61 and of the lug 43 to be accurately determined with an X ray, radiopaque markers 115 and 117 (FIGS. 4, 8 and 9) are provided in the overhang and the lug 43, respectively. Although various different constructions can be employed, in the embodiment illustrated, each of the radiopaque markers is in the form of a short metal pin of suitable radiopaque material embedded in the acetabular cup.

In use, the protrusio cup 13 can be implanted as a unit into the acetabulum 15 using the bone cement 17 and conventional techniques. As shown in FIGS. 1 and 2, the overhang 61 and the overhanging section 67 lie primarily in the superior-posterior region and have their maximum extension posteriorly of the most superior region. The presence of the overhanging section 67 in this region causes the protrusio cup 13 to resist dislocation. For example, the maximum extension may be displaced 30 degrees to 45 degrees from the most superior position. When so positioned, portions of the overhanging section 67 are also in the superior-anterior and inferior-posterior regions as shown in FIG. 2. The flanges 87, 89 and 91 are spaced circumferentially so that they engage the pubis 119, the ischium 121 and the iliac 123, respectively, to transfer loads to the bony region they engage.

The center of the femoral head 21 is substantially at the center 55 of the bearing surface 35. Because of the absence of the bearing surface 35 in the region represented by the dashed line 71 (FIG. 4), greater space is provided to accommodate motion of the neck 25, and hence a greater range of motion is obtainable. Rotation of the part-conical surface 47 also provides more space to accommodate movement of the neck 25 and, hence, increases the range of motion. Moreover, if the femoral head 21 rotates to position the neck 25 against the part-conical surface 47, essentially line contact, rather than point contact, is obtained. Accordingly, dislocation is less likely to occur.

Although an exemplary embodiment of the invention has been shown and described, many changes, modifications and substitutions may be made by one having ordinary skill in the art without necessarily departing from the spirit and scope of this invention.

I claim:

1. A protrusio cup which can be implanted as a unit in the acetabulum comprising:
    an acetabular cup adapted to be received within the acetabulum;
    said acetabular cup having an inner concave bearing surface of generally part-spherical configuration defining a cavity which opens at a mouth, said bearing surface being adapted to receive a femoral head and slidably cooperate therewith;

said acetabular cup having a resilient skirt on the exterior of the acetabular cup and a wall spaced radially inwardly of the skirt to define a gap between the skirt and the wall whereby the skirt can flex radially inwardly;

a protrusio shell having a generally annular segment receiving a generally annular region of the acetabular cup adjacent the mouth of the acetabular cup and flange means adjacent one end of the annular segment projecting generally radially of the annular segment and adapted to engage the bony region around the acetabulum, the other end of the annular segment of the protrusio shell being open with the acetabular cup extending through the opening;

means for mounting the protrusio shell on the acetabular cup prior to implantation whereby the acetabular cup with the protrusio shell mounted thereon can be implanted as a unit in the acetabulum;

said mounting means including interlocking means on the acetabular cup and the protrusio shell, a portion of the interlocking means being on said skirt; and said mounting means including a circumferentially extending groove formed in the exterior of the acetabular cup and lying entirely within the annular region of the acetabular cup which receives at least a portion of the annular segment of the protrusio shell.

2. A protrusio cup as defined in claim 1 wherein said skirt is continuous and annular.

3. A protrusio cup as defined in claim 1 wherein said portion of the annular segment of the protrusio shell includes a rib on said protrusio shell adapted to be received by said groove on said acetabular cup, said acetabular cup having a polar region and said skirt being between said polar region and said groove on said acetabular cup.

4. A protrusio cup as defined in claim 3 wherein said skirt is continuous and annular and said interlocking means includes a rib on the skirt projecting radially outwardly and an annular groove on the protrusio shell for receiving the rib on the skirt.

5. A protrusio cup as defined in claim 1 wherein the exterior of the annular segment of the protrusio shell has a plurality of grooves defining segments and said grooves are adapted to receive and interlock with cement to securely attach the protrusio cup within the acetabulum.

6. A protrusio cup as defined in claim 5 wherein said acetabular cup has grooves on the exterior thereof and at least some of said grooves of the acetabular cup are in alignment with at least some of the grooves of the protrusio shell.

7. A protrusio cup as defined in claim 1 wherein said flange means includes at least two spaced flanges and said acetabular cup has a peripheral flange, said peripheral flange has at least two notches for receiving said two flanges, respectively, and said notches and said flanges cooperate to at least assist in preventing relative rotation between the protrusio shell and the acetabular cup about a polar axis.

8. A protrusio cup as defined in claim 1 wherein said acetabular cup projects beyond said one end of the protrusio shell with said projection being greater on one side of the acetabular cup than on the other to define an overhang at least on said one side of the acetabular cup, said bearing surface at said one side of the acetabular cup projecting beyond said one end of said protrusio shell to define at least a portion of the inner surface of the overhang to reduce the likelihood of dislocation, said bearing surface at said other side of the acetabular cup terminating short of said one end of the protrusio shell to provide for an increased range of motion for the femoral head, and said acetabular cup has a part-conical surface which intersects said bearing surface and which widens as it extends away from said bearing surface to provide an increased range of motion.

9. A protrusio cup as defined in claim 8 wherein said part-conical surface having a cone angle and said cone angle being rotated generally away from said one side of the acetabular cup to provide an increased range of motion for the femoral head.

10. A protrusio cup as defined in claim 1 wherein said acetabular cup projects beyond said one end of the protrusio shell with said projection being greater on one side of the acetabular cup than on the other to define an overhang at least on said one side of the acetabular cup and a radiopaque marker in said overhang.

11. A protrusio cup for implantation in the acetabulum comprising:

an acetabular cup adapted to be received within the acetabulum;

said acetabular cup having an inner concave bearing surface of generally part-spherical configuration defining a cavity, said bearing surface being adapted to receive a femoral head and slidably cooperate therewith;

said acetabular cup having an outer surface;

a protrusio shell having a generally annular segment receiving an annular region of the acetabular cup and flange means adjacent one end of the annular segment projecting generally radially of the annular segment and adapted to engage the bony region around the acetabulum, the other end of the annular segment of the protrusio shell being open;

said acetabular cup having a projection which extends beyond said one end of the protrusio shell with said projection being greater on one side of the acetabular cup than on the other to define an overhang at least on said one side of the acetabular cup;

said bearing surface at said one side of the acetabular cup projecting beyond said one end of said protrusio shell to define at least a portion of the inner surface of the overhang to reduce the likelihood of dislocation;

said bearing surface at said other side of the acetabular cup terminating short of said one end of the protrusio shell to provide for an increased range of motion for the femoral head; and said acetabular cup having a part-conical surface which intersects said bearing surface and which widens as it extends away from said bearing surface to provide an increased range of motion.

12. A protrusio cup as defined in claim 11 wherein the bearing surface is substantially hemispherical.

13. A protrusio cup as defined in claim 11 wherein said part-conical surface has a cone angle and said cone angle is rotated generally away from said one side of the acetabular cup to provide an increased range of motion for the femoral head.

14. A protrusio cup as defined in claim 13 wherein said part-conical surface intersects said bearing surface at a first plane and terminates in a second plane which is nonparallel to said first plane, whereby said part-conical surface is shorter on said one side of said acetabular cup than on said other side of the acetabular cup.

15. A protrusio cup as defined in claim 13 wherein said bearing surface and said part-conical surface are rotated through approximately equal angles toward said one side of the acetabular cup.

16. A protrusio cup as defined in claim 15 wherein said angles are about 17 degrees.

17. A protrusio cup as defined in claim 11 wherein the acetabular cup is constructed of plastic and said protrusio cup includes a radiopaque marker in said overhang.

18. An acetabular cup having an outer surface and inner concave bearing surface of generally hemispherical configuration adapted to receive a femoral head, said acetabular cup having a part-conical surface which intersects said bearing surface to define a first plane and which terminates in a second plane which is nonparallel to said first plane, said part-conical surface extending radially outwardly as it extends from said first plane to said second plane, and said part-conical surface and said bearing surface being rotated through approximately equal angles generally in the direction in which the planes separate.

19. An acetabular cup as defined in claim 18 wherein said angles are about 17 degrees.

20. A protrusio cup for implantation in the acetabulum comprising:

an acetabular cup adapted to be received within the acetabulum;

said acetabular cup having an inner concave bearing surface of generally part-spherical configuration defining a cavity, said bearing surface being adapted to receive a femoral head and slidably cooperate therewith;

said acetabular cup having a resilient skirt on the exterior of the acetabular cup and a wall spaced radially inwardly of the skirt to define a gap between the skirt and the wall whereby the skirt can flex radially inwardly;

a protrusio shell having a generally annular segment receiving a generaally annular region of the acetabular cup and flange means adjacent one end of the annular segment projecting generally radially of the annular segment and adapted to engage the bony region around the acetabulum, the other end of the annular segment of the protrusio shell being open;

means for mounting the protrusio shell on the acetabular cup including interlocking means on the acetabular cup and the protrusio shell, a portion of the interlocking means being on said skirt; and said portion of said interlocking means including a rib on the skirt projecting radially outwardly and a groove on the protrusio shell for receiving the rib.

* * * * *